(12) United States Patent
Carter

(10) Patent No.: US 6,563,006 B2
(45) Date of Patent: May 13, 2003

(54) CATALYTIC OXIDATIVE CONVERSION OF HYDROCARBONS TO ALDEHYDES

(76) Inventor: Melvin K. Carter, P.O. Box 1852, Los Gatos, CA (US) 95031

(*) Notice: Subject to any disclaimer, the term of this patent is extended or adjusted under 35 U.S.C. 154(b) by 0 days.

(21) Appl. No.: 09/846,852

(22) Filed: Apr. 30, 2001

(65) Prior Publication Data

US 2002/0183559 A1 Dec. 5, 2002

(51) Int. Cl.⁷ .................. C07C 45/00; C07C 29/00; C07C 27/26; C07B 41/00; C07B 41/02
(52) U.S. Cl. ............... 568/449; 568/469.9; 568/470; 568/475; 568/909.5; 568/910.5; 568/915
(58) Field of Search .................. 568/449, 469.9, 568/470, 475, 909.5, 910.5, 915

(56) References Cited

U.S. PATENT DOCUMENTS

| | | | |
|---|---|---|---|
| 3,996,294 A | 12/1976 | Imre et al. | 260/604 R |
| 4,011,272 A | 3/1977 | Matsuzawa et al. | 260/641 |
| 4,013,729 A | 3/1977 | Suggitt et al. | 260/632 C |
| 4,045,498 A | 8/1977 | Deno | 260/617 R |
| 4,065,511 A | 12/1977 | Holtz | 260/635 R |
| 4,072,720 A | 2/1978 | Haag et al. | 260/618 H |
| 4,112,004 A | 9/1978 | Mabuchi et al. | 568/861 |
| 4,144,401 A | 3/1979 | Wall | 568/840 |
| 4,180,688 A | 12/1979 | Imaizumi et al. | 568/899 |
| 4,240,985 A | 12/1980 | Sheperd, Jr. | 568/483 |
| 4,270,011 A | 5/1981 | Okumura et al. | 568/899 |
| 4,296,262 A | 10/1981 | Grane et al. | 568/910 |
| 4,296,263 A | 10/1981 | Worrell | 568/910 |
| 4,306,084 A | 12/1981 | Pettit | 568/451 |
| 4,306,406 A | 12/1981 | Fulkerson et al. | 56/13.5 |
| 4,387,007 A | 6/1983 | Seiler | 204/59 R |
| 4,408,085 A | 10/1983 | Gottlieb et al. | 568/697 |
| 4,450,301 A | 5/1984 | McMillan et al. | 568/473 |
| 4,454,354 A | 6/1984 | Ferris et al. | 568/473 |
| 4,456,776 A | 6/1984 | Neier et al. | 568/899 |
| 4,459,427 A | 7/1984 | Middleton et al. | 568/342 |
| 4,469,903 A | 9/1984 | Schmidt | 568/918 |
| 4,474,996 A | 10/1984 | Carcia et al. | 568/473 |
| 4,476,333 A | 10/1984 | Neier et al. | 568/899 |
| 4,484,013 A | 11/1984 | Schmidt | 568/899 |
| 4,501,910 A | 2/1985 | Delmas et al. | 549/506 |
| 4,537,909 A | 8/1985 | Lin et al. | 518/713 |
| 4,544,773 A | 10/1985 | Sagou | 568/487 |
| 4,551,444 A | 11/1985 | Lin et al. | 502/313 |
| 4,560,672 A | 12/1985 | Attig et al. | 502/183 |
| 4,562,297 A | 12/1985 | Roper | 568/432 |
| 4,607,505 A | 8/1986 | Grazioso et al. | 518/713 |
| 4,705,771 A | 11/1987 | Spencer | 502/255 |
| 4,847,424 A | 7/1989 | Matsushita et al. | 568/484 |
| 4,857,664 A | 8/1989 | Huang et al. | 568/695 |
| 4,859,799 A | 8/1989 | Campestrini et al. | 568/430 |
| 4,885,412 A | 12/1989 | Pennington et al. | 568/469.9 |
| 4,910,349 A | 3/1990 | Sanderson et al. | 568/909.8 |
| 4,956,392 A | 9/1990 | Saito et al. | 518/712 |
| 4,956,506 A | 9/1990 | Latimer | 568/899 |
| 5,409,877 A | 4/1995 | Takeuchi et al. | 502/245 |
| 5,414,145 A | 5/1995 | Sheu et al. | 568/671 |
| 5,426,238 A | 6/1995 | Mori et al. | 568/454 |
| 5,602,280 A | 2/1997 | Nagai et al. | 562/546 |
| 5,623,090 A | 4/1997 | Haruta et al. | 568/360 |
| 5,698,744 A | 12/1997 | Lee | 568/322 |
| 5,856,585 A | 1/1999 | Sanfilippo et al. | 568/470 |
| 5,990,358 A | 11/1999 | Knuth et al. | 568/473 |
| 6,028,228 A | 2/2000 | Wachs | 568/482 |
| 6,069,282 A | 5/2000 | Fritz-Langhals et al. | 568/320 |
| 6,084,135 A | 7/2000 | Wachs | 568/482 |
| 6,143,928 A | 11/2000 | Karim et al. | 562/534 |
| 6,147,263 A | 11/2000 | Wachs et al. | 568/473 |

Primary Examiner—Samuel Barts
Assistant Examiner—Sikarl A. Witherspoon

(57) ABSTRACT

Catalytic processes have been developed for direct ambient air oxidative conversion of hydrocarbons to aldehydes and unsaturated alcohols. Aliphatic hydrocarbons including methane, hexanes, octanes, decanes, gasoline, diesel fuel, oils, solvents and other organic compounds have been oxidized by this catalytic process. The catalysts are based on molecular strings of di-, tri- and/or poly-groups of transition metal complexes. Laboratory results have demonstrated $[iron(II)]_2$, $[manganese(II)]_2$ and related families of catalysts to be effective for ambient air direct oxidative conversion of hydrocarbons to products in high yields at room temperature and above, while $[cobalt(II)]_3$ was effective for air oxidative conversion of methane to formaldehyde and for other gaseous hydrocarbons to their corresponding aldehydes at elevated temperatures.

14 Claims, No Drawings

CATALYTIC OXIDATIVE CONVERSION OF HYDROCARBONS TO ALDEHYDES

BACKGROUND—FIELD OF INVENTION

This invention relates to ambient air catalytic oxidation of saturated hydrocarbons, specifically to efficient catalytic oxidative conversion of hydrocarbons to aldehydes and unsaturated alcohols employing catalysts based on molecular strings of di-, tri- and/or poly-groups of bonded transition metal complexes.

BACKGROUND—DESCRIPTION OF PRIOR ART

A number of chemical reaction paths have previously been investigated for single step conversion of aliphatic hydrocarbons to aldehydes or alcohols but none teach high conversion efficiencies without employment of high temperature and pressure, aggressive chemical oxidizers or strong chemical agents. For example, controlled oxidation of methane, investigated under a wide range of conditions, has produced carbon dioxide, carbon monoxide, low concentrations of unsaturated hydrocarbons, oligomers, low levels of alcohols, aldehydes and water. None of these efforts have produced significant amounts of aldehydes or alcohols. As a result direct conversion of saturated hydrocarbons to aldehydes and/or alcohols has essentially been abandoned in favor of conversion of more labile hydrocarbons such as alkenes or other organic compounds with reactive groups. The invention disclosed in this application teaches catalytic air oxidative conversion of aliphatic hydrocarbons directly to aldehydes and unsaturated alcohols at room temperature and above using di-metal, tri-metal and/or poly-metal backbone or molecular string type transition metal catalysts without addition of aggressive chemical oxidizing agents and without addition of other strong chemicals. No labile or other reactive chemical groups are required for production of aldehydes and unsaturated alcohols from saturated hydrocarbons. Use of di-metal, tri-metal and/or poly-metal backbone or molecular string type transition metal catalysts described in this application produce a significantly higher yield of oxidized products than the relatively inactive mono-metal transition metal compounds.

Air oxidation of hydrocarbon vapors has been accomplished in pressurized reactions at elevated temperatures in the presence of selected transition metal salts or on the surface of shaped pore solid zeolites. Olefin or alkenyl type unsaturated hydrocarbons may be oxidized to aldehydes with air or oxygen at elevated temperatures in the presence of transition metal compounds as taught in the following patents. U.S. Pat. No. 6,143,928, issued Nov. 7, 2000, teaches of the catalytic oxidation of propylene with molecular oxygen containing gas at 100° C. to 450° C. and 1 to 50 bars pressure. U.S. Pat. No. 6,069,282, issued May 30, 2000, discloses preparation of vinyl, alkynyl or aryl aldehydes by reaction of vinyl, alkynyl or aryl-methanols with the aid of a mediator and an oxidant, wherein the mediator is selected from the group of aliphatic, cycloalphatic, heterocyclic or aromatic NO or NOH containing compounds. U.S. Pat. No. 5,426,238, issued Jun. 20, 1995, introduces a method for producing an aldehyde, which comprises reacting an olefin with carbon monoxide and hydrogen in a hydroformulation reaction in the presence of a rhodium catalyst with an organophosphorus ligand. U.S. Pat. No. 5,409,877, issued Apr. 25, 1995, demonstrates another method for production of an aldehyde and an alcohol using a heterogeneous transition metal catalyst for the hydroformylation of an olefin with $H_2$ and CO. These disclosures employ the labile olefinic double bond as a reaction site for selective oxidation but do not describe a method for convenient conversion of saturated hydrocarbons to aldehydes.

Strong chemical oxidizing agents have also been employed for controlled oxidative conversion of alcohols, alkenes and other labile compounds to aldehydes and other products under controlled conditions. U.S. Pat. No. 5,698,744, issued Dec. 16, 1997, shows a process for the selective oxidation employing ferromagnetic chromium dioxide. U.S. Pat. No. 5,602,280, issued Feb. 11, 1997, formed an unsaturated aldehyde and an unsaturated carboxylic acid by subjecting propylene, isobutylene or tertiary butanol to gas phase catalytic oxidation with molecular oxygen in the presence of transition metal oxides including tungsten oxides followed by re-oxidation of the transition metal oxide to its original oxidation state. Here the metal oxides may be considered to be co-reactants since they require re-oxidation by oxygen gas to be converted back to their beginning state. U.S. Pat. No. 4,885,412, issued Dec. 5, 1989, teaches a process for producing an aldehyde from alkylaromatics in the vapor phase in the presence of molten nitrate salt catalysts. Here the term catalyst has been used to indicate the necessity for a chemical oxidizer in the form of a molten nitrate. U.S. Pat. No. 4,859,799, issued Aug. 22, 1989, introduced a process for production of aldehydes or ketones by oxidative cleavage of olefinic double bonds by means of a coordination complex of a ligand and a peroxo derivative of a transition metal. Even electrochemical techniques have been employed to drive oxidative reactions of organic compounds as described in U.S. Pat. No. 4,387,007, issued Jun. 7, 1983, in which para-tertiary-butylbenzaldehyde was manufactured by the electrochemical oxidation of para-tertiary-butyltoluene. These chemical reactions required the oxidizing power of strong chemical oxidizing agents or electrochemistry to achieve product aldehydes.

Strong chemicals such as strong acids and strong base hydroxides have also been used to achieve conversion of labile compounds to aldehydes. U.S. Pat. No. 4,562,297, issued Dec. 31, 1985, teaches that 3,5-dihydrocarbyl-4-hydroxybenzaldehydes are prepared from 4-(1-alkyenyl)-2,5-dihydrocarbylphenol, such as 1,1-dimethyl-2-(3,5-di-ter-t-butyl-4-hydroxyphenyl)ethene, with at least a stoichiometric amount of an oxygen-containing gas at 50° C. to 250° C. in the presence of an alcohol solvent and a catalytic amount of an alkali or alkaline earth metal hydroxide. U.S. Pat. No. 4,240,985, issued Dec. 23, 1980, produced aldehydes by cleaving 2,2-dialkyltetrahydropyrans bearing two hydrogen atoms in the sixth position using a strong acid. Thus, it is apparent that there are three classes of existing processes for preparation of aldehydes with mono-transition metal compounds: one class converts labile groups, including unsaturated or olefinic compounds with or without hydrogen, alcohols and other labile groups to aldehydes by chemical conversion. A second process class employs strong chemical oxidizing agents, such as permanganates, chromates, perchlorates, peroxides, chromium oxides and other oxygen rich chemical agents at elevated temperature to produce aldehydes. A third class of processes uses strong acids or strong bases to affect chemical conversion in the production of selected aldehydes. None of these patents teach how to convert saturated hydrocarbons to aldehydes at ambient conditions.

Olefins or unsaturated hydrocarbons can also be oxidized to alcohols with oxygen or by strong chemical means, usually at elevated temperatures and pressures, in the presence or absence of transition metal compounds. U.S. Pat. No. 5,623,090 issued Apr. 22, 1997, U.S. Pat. No. 5,414,145 issued May 9, 1995 and U.S. Pat. No. 4,296,262 issued Oct. 20, 1981 oxidized olefins with oxygen to form alcohols, while U.S. patent issued Aug. 30, 1977 and U.S. Pat. No. 4,013,729 issued Mar. 22, 1977 oxidized olefins by strong chemical means. Olefins can also be hydrolyzed to produce alcohols as taught in U.S. Pat. No. 4,956,506 issued Sep. 11, 1990, U.S. Pat. No. 4,857,664 issued Aug. 15, 1989, U.S. Pat. No. 4,484,013 issued Nov. 20, 1984, U.S. Pat. No. 4,476,333 issued Oct. 9, 1984, U.S. Pat. No. 4,469,903 issued Sep. 4, 1984, U.S. Pat. No. 4,456,776 issued Jun. 26, 1984, U.S. Pat. No. 4,408,085 issued Oct. 4, 1983, U.S. Pat. No. 4,360,406 issued Nov. 23, 1982, U.S. Pat. No. 4,306,084 issued Dec. 15, 1981, U.S. Pat. No. 4,296,263 issued Oct. 20, 1981, U.S. Pat. No. 4,270,011 issued May 26, 1981 and U.S. Pat. No. 4,180,688 issued Dec 25, 1979.

Carbonylation has been invoked under various conditions for the production of alcohols as in U.S. Pat. No. 4,956,392 issued Sep. 11, 1990, U.S. Pat. No. 4,607,055 issued Aug. 19, 1986, U.S. Pat. No. 4,560,672 issued Dec. 24, 1985, U.S. Pat. No. 4,551,444 issued Nov. 5, 1985, U.S. Pat. No. 4,537,909 issued Aug. 27, 1985, U.S. Pat. No. 4,144,401 issued Mar. 13, 1979 and U.S. Pat. No. 4,072,720 issued Feb. 7, 1978.

Hydrocarbons have also been chemically oxidized forming peroxides which were subsequently converted to alcohols as shown in U.S. Pat. No. 4,910,349 issued Mar. 20, 1990, U.S. Pat. No. 4,910,349 issued Mar. 20, 1990, U.S. Pat. No. 4,112,004 issued Sep. 5, 1978 and U.S. Pat. No. 4,065,511 issued Dec. 27, 1977. Thus, it is apparent that many of the processes employed for the production of aldehydes have also been modified for the production of alcohols. None of these patents teach direct oxidative conversion of saturated aliphatic hydrocarbon to aldehydes and unsaturated alcohols without use of aggressive chemical oxidizing agents or other strong chemical means.

Formaldehyde has been formed in low yields by oxidizing methane with oxygen or by strong chemical means, usually at elevated temperatures and pressures, in the presence of transition metal compounds. U.S. Pat. No. 5,856,585 issued Jan. 5, 1999, U.S. Pat. No. 4,705,771 issued Nov. 10, 1987 and U.S. Pat. No. 3,996,294 issued Dec. 7, 1976 oxidized methane with oxygen to form formaldehyde in yields of less than ten percent.

Methanol has been dehydrogenated under various conditions in the gas phase for the production of formaldehyde as in U.S. Pat. No. 6,147,263 issued Nov. 14, 2000, U.S. Pat. No. 5,990,358 issued Nov. 23, 1999, U.S. Pat. No. 4,544,773 issued Oct. 1, 1985, U.S. Pat. No. 4,474,996 issued Oct. 2, 1984, U.S. Pat. No. 4,454,354 issued Jun. 12 and 1984, U.S. Pat. No. 4,450,301 issued May 22, 1984. These patents invoke labile hydrocarbons for production of formaldehyde as opposed to starting with aliphatic hydrocarbons.

The invention disclosed in this application is different from the classifications referenced above in that aliphatic hydrocarbons are catalytically, directly air oxidized at room temperature and above using di-metal, tri-metal and/or poly-metal backbone or molecular string type transition metal catalysts without addition of aggressive chemical oxidizing agents and without addition of other strong chemicals. In addition, hydrocarbons can be oxidized with equal molar amounts of air to form aldehydes in high yields. No labile or other reactive chemical groups are required for production of aldehydes and unsaturated alcohols from saturated hydrocarbons.

Direct air oxidation catalysts of the di-metal, tri-metal and/or poly-metal backbone type, employed in the title invention, have facilitated oxidation processes of hydrocarbons at ambient conditions wherein aldehydes and unsaturated alcohols products were formed while mono-metal compounds were ineffective. For example, a process comprising a stirred aqueous mixture containing 14,000 ppm n-decane at a temperature of 16° C. was oxidized in air, using an [iron(II)]$_2$ catalyst thereby reducing the n-decane reactant to a concentration of <900 ppm in five hours. Furthermore, a stirred aqueous mixture containing hexanes at ambient temperature was oxidized in air using related catalysts thereby reducing the concentration in a similar fashion. These same molecular string catalysts are also effective in oxidizing gasoline and diesel fuel in soil at ambient conditions. For example, 100 mg/kg of gasoline and 100 mg/kg of diesel fuel in soil have been air oxidized in 15 to 20 days reducing the hydrocarbon concentrations to less than 1 mg/kg forming aldehydes and other products. This ambient temperature air oxidation of hydrocarbons can be of value in eliminating such spilled hydrocarbons from a chemically sensitive environment. In addition, methane gas has been catalytically oxidized to formaldehyde and water vapor in yields in excess of 90 percent at elevated temperatures over a [cobalt (II)]$_3$ catalyst. In each case use of the respective mono-metal catalyst produced no detectable oxidized products.

Selective use of different di-, tri- and/or poly-groups of transition metal catalysts are employed in the catalytic process for production of mono-and di-aldehydes and unsaturated alcohols. For example, primary and secondary aliphatic hydrocarbons, and such aliphatic groups that may be attached to alkenes, aromatics and other non-aliphatic moieties, can be catalytically air oxidized to convert the hydrocarbon or alkyl groups to aldehydes. Similarly, tertiary aliphatic hydrocarbons can be catalytically air oxidized to convert the hydrocarbon or alkyl groups to alcohols. Similarly, methane has been oxidatively converted to formaldehyde by this same process.

It is an object of this invention, therefore, to provide a molecular string type transition metal catalytic process for air oxidative conversion of aliphatic hydrocarbons, and alkyl groups attached to other compounds, to aldehydes and unsaturated alcohols.

It is another object of this invention to provide molecular string type catalysts for direct ambient air oxidation of hydrocarbons including hexanes, octanes, decanes, hydrocarbon oils, solvents, gasoline, jet fuel, diesel fuel, heating and lubricating oils, mineral spirits and other solvent type hydrocarbons.

It is another object of this invention to provide a molecular string type catalytic process for direct oxidative conversion of hydrocarbon reactants to aldehydes and unsaturated alcohol products without use of aggressive chemical oxidizing agents or other strong chemicals. Other objects of this invention will be apparent from the detailed description thereof which follows, and from the claims.

SUMMARY OF THE INVENTION

This invention describes a chemical process using any member of a family of transition metal catalysts, based on a di-metal, tri-metal and/or poly-metal backbone or string, for oxidation of aliphatic hydrocarbons at ambient temperature and above producing aldehydes and unsaturated alcohols. These catalysts have been effectively demonstrated to be active for oxidation of linear and branched hydrocarbons.

DETAILED DESCRIPTION OF THE INVENTION

The process for catalytic oxidation of hydrocarbons to aldehydes and unsaturated alcohols in high yields is based on catalysts possessing multiple metal type transition metal compounds, such as [iron]$_2$ or [manganese]$_2$ type compounds. These catalysts have been designed based on a formal theory of catalysis, and the catalysts have been produced, and tested to prove their activity. The theory of catalysis rests upon a requirement that a catalyst possess a linear backbone or molecular string such that transitions from one molecular electronic configuration to another be essentially barrier free so reactants may proceed freely to products. Catalysts effective for ambient air oxidation of hydrocarbons can be made from di-metal, tri-metal and/or poly-metal backbone or molecular string type compounds of the transition metals, comprising titanium, manganese, iron, cobalt, nickel, copper, molybdenum, ruthenium, rhodium, palladium, silver, tungsten, rhenium, osmium, iridium, platinum, gold and combinations thereof These catalysts are made in the absence of oxygen so as to produce compounds in the divalent state or other low oxidation state. Anions employed for these catalysts comprise chloride, bromide, cyanide, isocyanate, thiocyanate, metal cyanides, sulfate, phosphate, oxide, oxalate and other more complex groups, only some of which are found to be non-toxic to the natural environment. Mixed transition metal compounds have also been found to be effective catalysts for ambient air oxidation of organic compounds. For example, compounds containing a iron(II).copper(I) backbone or bond are also effective for oxidization of hydrocarbons using ambient air.

Numerous different Cu.Fe, [iron]$_2$, [iron]$_3$, [manganese]$_2$ and related oxidation catalysts have been prepared for air oxidation of n-decane in water at ambient pressure and at a temperature of 0° C. and above. These same catalysts were effective for oxidation of 20 ppm gasoline, 100 ppm diesel fuel, 200 ppm hexanes and pure n-decane in water with use of atmospheric air. Oxidation reactions can be conducted in ambient air at room temperature in an open top stirred container converting the hydrocarbons to aldehydes in yields in excess of seventy percent. In addition, several [iron]$_2$ catalysts have proven to be efficient for complete oxidation of gasoline and/or diesel fuel in soil. Vapor phase reactions have been conducted at elevated temperature using a tube type reactor and [cobalt]$_3$ catalysts for ambient air oxidative conversion of methane to formaldehyde in yields in excess of ninety percent based on methane.

Catalyst Selection Considerations

The fundamentals of catalysis effort forms a basis for selecting molecular catalysts for specified chemical reactions through computational methods by means of the following six process steps. An acceptable oxidation mechanism, involving two sets of pairs of metal atoms, was established for oxygen gas in the presence of water (step 1). A specific transition metal, such as iron, was selected as a possible catalytic site as found in an M—M or Fe—Fe string (step 2), bonded with four oxygen molecules in a $D_{4h}$ point group symmetry configuration, and having a computed bonding energy to the associated oxygen reactants of less than −60 kcal/mol (step 3). The first valence state for which the energy values were two-fold degenerate was 2+ (step 4). Cyanide, chloride and other anions may be chosen provided they are chemically compatible with the metal, M (Fe), in formation of the catalyst (step 5). A test should also be conducted to establish compliance with the rule of 18 (or 32) to stabilize the catalyst so compatible ligands may be added to complete the coordination shell (step 6). This same process may be applied for selection of a catalyst using any of the first, second or third row transition metals, however, only those with acceptable low positive or negative bonding energies can produce effective catalysts. The approximate, computed, relative bonding energy values may be computed using a semi-empirical algorithm. This computational method indicated that any of the first row transition metal oxygen complexes can produce usable catalysts once the outer coordination shell had been completed with ligands, even though the elements Ti, Mn, Fe, Co, Ni and Cu indicated reasonable bonding energies in a simplified molecular model. Second row transition metal oxygen complexes based on Mo, Ru, Rh, Pd and Ag are indicated to produce active oxidation catalysts. Third row transition metal oxygen complexes are all indicated to produce active oxidation catalysts. In general, preliminary energy values computed for transition metal oxygen complexes are indicated to produce useable catalysts once bonding ligands have been added.

Description of Catalyst Preparation and Hydrocarbon Oxidation

Catalyst preparation has been conducted using nitrogen sparging and nitrogen blanketing to minimize or eliminate air oxidation of the transition metal compounds during preparation. Transition metal catalysts, effective for ambient air oxidation of organic compounds, can be produced by combining transition metal salts in their lowest standard oxidation states. Thus, such transition metal catalysts can be made by reacting alkali metal salts of transition metal(I or II) cyanides with transition metal(I or II) chlorides or bromides in a 1 to 1 or 1 to 2 ratio, or by forming transition metal compounds in a reduced state by similar means where di-, tri- and/or poly-metal compounds result.

EXAMPLE 1

Preparation of the Fe(CN)$_2$L.FeCl$_2$L catalyst, for L being K$_3$Cu(CN)$_4$, was conducted by a process similar to that described above. To 0.3583 gram (0.004 mol) of copper (I) cyanide was added 0.7815 gram (0.012 mol) of potassium cyanide dissolved in minimal deionized water. The mixture was heated to just below boiling until a clear solution of K$_3$Cu(CN)$_4$ formed. This solution was set aside for later use. A 1 mL solution containing 0.2605 gram (0.004 mol) of potassium cyanide was added to a 10 mL solution of 0.3976 gram (0.002 mol) of FeCl$_2$.4H$_2$O with agitation from bubbling nitrogen. A red-orange colored suspension formed. To this was added a second solution of 0.3976 gram of FeCl$_2$.4H$_2$O with agitation. The K$_3$Cu(CN)$_4$ solution, prepared previously, was added to the resulting suspension producing a yellow colored catalyst suspension. The solid was acidified with 0.218 gram of 75 percent phosphoric acid, was allowed to settle, was drained, washed with five 30 mL portions of nitrogen purged water, drained again and dried under vacuum producing a bright yellow solid. This catalyst is most often precipitated onto solid silica or other heterogeneous support for vapor phase oxidations.

EXAMPLE 2

Preparation of the Mn(CN)$_2$L.MnCl$_2$L catalyst, for L being K$_3$Cu(CN)$_4$, was conducted as described herein. To 0.3583 gram (0.004 mol) of copper (I) cyanide was added 0.7815 gram (0.012 mol) of potassium cyanide dissolved in minimal deionized water. The mixture was heated to just below boiling until a clear solution of K$_3$Cu(CN)$_4$ formed. This solution was set aside for later use. A 1 mL solution containing 0.2605 gram (0.004 mol) of potassium cyanide was added to a 10 mL solution of 0.3958 gram (0.002 mol) of MnCl$_2$.4H$_2$O with agitation from bubbling nitrogen. A solid suspension formed. To this was added a second solution of 0.3958 gram of MnCl$_2$.4H$_2$O with agitation followed by addition of the $K_3Cu(CN)_4$ solution, prepared previously producing the catalyst suspension. The solid was acidified with 0.218 gram of 75 percent phosphoric acid, was allowed to settle, was drained, washed with five 30 mL portions of nitrogen purged water, drained again and dried under vacuum producing a solid catalyst.

The solid [iron(II)]$_2$ catalyst of example 1 was used to air oxidize n-decane in water. A 100 mL portion of DI water was added to a 250 mL beaker and 1.42 grams of n-decane oil (10 mmols, 14,000 ppm) was weighed into the water. The solid [iron(II)]$_2$ catalyst was prepared as described and 1 mmol of the catalyst suspension was dispersed in the water to start the reaction as the mixture was stirred rapidly and maintained at 15° C. to 17° C. at atmospheric pressure. Twelve 1 mL samples were collected during the first five hours of the run. At the end of each five hour segment an additional 1.42 grams (10 mmols) of n-decane was added for a total of nine additions of n-decane. Samples were also collected just prior to each addition of n-decane. Each 1 mL sample was immediately extracted by vigorous agitation with 2 mL of reagent grade dichloromethane for 30 seconds. The concentrations of residual n-decane and oxidized hydrocarbon products were measured by a GC procedure for each extract.

At the end of the first five hours of catalytic oxidation the concentration of n-decane was measured as <900 ppm indicating catalytic oxidative conversion of more than ninety percent efficiency. This reaction was continued with additions of 1.42 grams of n-decane following each additional five-hour reaction period with similar results. Termination of catalytic oxidation (after nine additions of n-decane) demonstrated a total of 12.78 grams (90 mmols) of n-decane had been added and 1 mmol of catalyst had caused approximately 11 grams (approximately 80 mmols) of n-decane (the remainder was lost due to evaporation or mechanical agitation) to be air oxidized with no measurable degradation in reaction rate. Analysis of oxidized n-decane by GC-MS procedures demonstrated formation of a mixture of complex products similar to those identified in hexane catalytic oxidation residues, including mono-, di- and tri-aldehydes and unsaturated alcohols in the $C_6$ through $C_{28}$ molecular weight range. A complex chemistry of oxidation, concatenation and bond scission of the original hydrocarbon compounds was facilitated by catalytic air oxidation using a solid [iron(II)]$_2$ catalyst. Catalysts prepared with bulkier ligands were designed to yield more selective oxidative conversion of hydrocarbons to mono- and di-aldehydes with efficiencies of greater than fifty percent.

EXAMPLE 3

A green colored solid [iron(II)]$_2$ oxalate catalyst was produced on a course zeolite mineral support. This catalyst turned a bright orange color when exposed to ambient air. To 100 pounds of mineral was added 2 pounds of an alkali metal oxalate ($Na_2C_2O_4$) followed by 3 pounds of iron(II) chloride ($FeCl_2$) and 2–3 pounds of an amine under nitrogen. The catalyst was dried during a period of 4 to 8 hours. To eight pounds of dry soil was added 0.36 gram of gasoline, to prepare a concentration of 100 mg/kg gasoline in soil, and 50 grams of dry, granular catalyst. The soil was mixed and 0.5 to 0.6 Liter of water was added. The treated soil resided in ambient air at approximately 15° C. to 17° C. for the duration of the tests. Samples were collected, extracted and tested for gasoline concentration several times each week for a period of three weeks. The soil was turned over, exposing it to air, following each sample collection. At the end of seventeen days the gasoline concentration was measured at less than 1 mg/kg indicating oxidative conversion efficiency of greater than ninety percent. A second soil sample was treated using the same protocol except no catalyst was added thereto. At the end of seventeen days the gasoline concentration measured approximately 25 mg/kg.

EXAMPLE 4

A sample of number 2 diesel fuel was similarly oxidized at 15° C. to 17° C. and ambient air pressure using the di-iron catalyst of example 3 above. To eight pounds of dry soil was added 0.36 gram of diesel fuel, to prepare a concentration of 100 mg/kg diesel fuel in soil, and 50 grams of dry, granular catalyst. The soil was mixed and 0.5 to 0.6 Liter of water was added. The treated soil resided in ambient air at approximately 15° C. to 17° C. for the duration of the tests. Samples were collected, extracted and tested for diesel fuel concentration several times each week for a period of four weeks. At the end of seventeen days the diesel fuel concentration was measured at less than 1 mg/kg indicating oxidative conversion efficiency of greater than ninety percent. A second soil sample was treated using the same protocol except no catalyst was added thereto. At the end of seventeen days the diesel fuel concentration measured approximately 60 mg/kg.

EXAMPLE 5

Methane was catalytically oxidized to formaldehyde over a tri-cobalt catalyst. Methane gas flow rate was set at 6.0 L/hour and the oxygen (from air) flow rate was 2.6 L/hour, a tube reactor was packed with a 5 percent $[CoO]_3$ catalyst on a silica support and set to a temperature of 600° C. The air inlet source was split into two lines staggered in the catalytic reaction zone so local concentrations of air did not exceed the combustion limits of methane. Formaldehyde in water was isolated and analyzed demonstrating over ninety percent conversion of methane to formaldehyde in a flow through or single pass mode.

Catalytic Oxidative Conversion

Catalytic ambient air oxidative conversion of liquid hydrocarbons to aldehydes and unsaturated alcohols has been demonstrated. The present effort has been focused on controlled oxidative conversion of aliphatic hydrocarbons to mono-aldehydes and di-aldehydes. This may be accomplished by limiting the amount of the reactant oxygen to that molar ratio necessary for formation of the desired products, however it may be most effectively accomplished using a catalyst whose access is restricted by means of bulky ligands. Reactions have been run at various temperatures converting hydrocarbons like n-hexane to aldehydes using the Fe.Fe and Mn.Mn catalysts. These catalysts had similar reaction rates but produced slightly different aldehyde products.

Vapor phase oxidations have been conducted in a continuous mode where hydrocarbons are vaporized and passed through the catalyst bed in the presence of oxygen in the 0° C. to 660° C. range. Some catalysts are preferred over others that were found to be more stable at elevated temperature. For example, the Fe.Fe catalysts were preferred at ambient temperatures while Mn.Mn and Co.Co.Co catalysts were preferred at elevated temperatures. Catalysts can be added to the hydrocarbon liquids in the form of aqueous suspensions but vapor phase oxidation's use supported catalysts in a fixed or a fluidized bed where hydrocarbon vapors, steam, oxygen and a carrier gas such as nitrogen (where an inert carrier is beneficial) are passed through the catalyst. Unconverted hydrocarbons can be vaporized for recycle. The degree of product formation may be controlled by addition of stoichiometric amounts of oxygen. Thus, formation of di-aldehydes would require twice the amount of oxygen as would mono-aldehydes, so long as the combustion limits of the hydrocarbon gas were not exceeded. Oxidative conversion processes can proceed to products considerably faster in the vapor phase so this reaction mode is indicated to be potentially more economical. Thus, a vapor phase process can convert aliphatic hydrocarbons to aldehydes in one or two rapid passes while a liquid conversion may require several hours of agitation. For example, methane combined with fractional to equal molar concentrations of oxygen over a Co.Co.Co backbone or molecular string type catalyst produced greater than 90 percent yields of formaldehyde and water in a single pass in the temperature range of 500° C. to 660° C., preferably in the temperature range of 550° C. to 650° C.

What is claimed:

1. A process for catalytic oxidative conversion of aliphatic hydrocarbons to aldehydes and/or unsaturated alcohols using air or oxygen and catalysts made from di-metal, tri-metal and/or poly-metal backbone or molecular string type compounds of transition metals, comprising titanium, vanadium, chromium, manganese, iron, cobalt, nickel, copper, molybdenum, ruthenium, rhodium, palladium, silver, hafnium, tantalum, tungsten, rhenium, osmium, iridium, platinum, gold and combinations thereof.

2. A process for catalytic oxidative conversion, of greater than twenty five percent efficiency, for aliphatic hydrocarbons to aldehydes and/or unsaturated alcohols using air or oxygen and catalysts made from di-metal, tri-metal and/or poly-metal backbone or molecular string type compounds of transition metals, comprising titanium, vanadium, chromium, manganese, iron, cobalt, nickel, copper, molybdenum, ruthenium, rhodium, palladium, silver, hafnium, tantalum, tungsten, rhenium, osmium, iridium, platinum, gold and combinations thereof.

3. A process as described in claim 1 above for temperatures in the range of 0° C. to 660° C.

4. A process as described in claim 1 above for oxidation of gasoline, diesel fuel, mineral spirits, jet fuel, kerosene, lubricating oil and other petroleum hydrocarbons.

5. A process as described in claim 1 above for oxidation of methane, natural gas, ethane, propane, butane and other hydrocarbon gases, for temperatures in the range of 0° C. to 660° C.

6. A process as described in claim 1 above for oxidative conversion of methane, natural gas, ethane, propane, butane and other hydrocarbon gases, for temperatures in the range of 0° C. to 660° C., to aldehydes and/or unsaturated alcohols.

7. A process as described in claim 2 above for temperatures in the range of 0° C. to 660° C.

8. A process as described in claim 2 above including compounds containing aliphatic groups.

9. A process as described in claim 2 above for oxidation of gasoline, diesel fuel, mineral spirits, jet fuel, kerosene, lubricating oil and other petroleum hydrocarbons.

10. A process as described in claim 2 above for oxidation of gasoline, diesel fuel, mineral spirits, jet fuel, kerosene, lubricating oil and other petroleum hydrocarbons for temperatures in the range of 0° C. to 660° C.

11. A process as described in claim 2 above for oxidation of methane, natural gas, ethane, propane, butane and other hydrocarbon gases, for temperatures in the range of 0° C. to 660° C.

12. A process as described in claim 2 above for oxidative conversion of methane, natural gas, ethane, propane, butane and other hydrocarbon gases, for temperatures in the range of 0° C. to 660° C., to aldehydes and/or unsaturated alcohols.

13. A process for catalytic oxidation of aliphatic hydrocarbons and compounds containing aliphatic groups to aldehydes and/or unsaturated alcohols using catalysts made from di-metal, tri-metal and/or poly-metal backbone or molecular string type transition metal compounds.

14. The process of claim 1, wherein the aliphatic hydrocarbon comprises gasoline, diesel fuel, mineral spirits, jet fuel, kerosene or lubricating oil.

* * * * *